US012393317B2

(12) United States Patent
Mandal et al.

(10) Patent No.: US 12,393,317 B2
(45) Date of Patent: Aug. 19, 2025

(54) SIMULATION SYSTEM FOR VIRTUAL HUMAN-BODY DISSECTION AND METHOD FOR SIMULATING VIRTUAL HUMAN-BODY DISSECTION

(71) Applicant: IMMERSIVEVISION TECHNOLOGY PVT. LTD., Pune (IN)

(72) Inventors: Navin Mandal, Mumbai (IN); Amit Ranjan, Pune (IN); Amresh Kumar, Mumbai (IN); Sneha Adsule, Pune (IN)

(73) Assignee: IMMERSIVEVISION TECHNOLOGY PVT. LTD. (IN)

( * ) Notice: Subject to any disclaimer, the term of this patent is extended or adjusted under 35 U.S.C. 154(b) by 0 days.

(21) Appl. No.: 18/638,679

(22) Filed: Apr. 18, 2024

(65) Prior Publication Data
US 2025/0094015 A1 Mar. 20, 2025

(30) Foreign Application Priority Data
Sep. 14, 2023 (IN) .............................. 202321062015

(51) Int. Cl.
*A61B 34/00* (2016.01)
*G06F 3/04815* (2022.01)
*G06F 3/0482* (2013.01)
*G06T 19/00* (2011.01)
*G09B 5/02* (2006.01)
*A61B 1/00* (2006.01)

(52) U.S. Cl.
CPC ........ *G06F 3/04815* (2013.01); *G06F 3/0482* (2013.01); *G06T 19/00* (2013.01); *G09B 5/02* (2013.01); *A61B 1/00* (2013.01); *A61B 34/00* (2016.02); *G06T 2210/41* (2013.01); *G06T 2219/004* (2013.01)

(58) Field of Classification Search
CPC ... G06F 3/04815; G06F 3/0482; G06T 19/00; G09B 5/02; A61B 34/00
See application file for complete search history.

(56) References Cited

U.S. PATENT DOCUMENTS

2010/0063788 A1* 3/2010 Brown .................... G06T 19/00
703/6
2018/0098813 A1 4/2018 Nesichi et al.
(Continued)

FOREIGN PATENT DOCUMENTS

WO 2020148643 A1 7/2020

*Primary Examiner* — Roy P Rabindranath

(57) ABSTRACT

The simulation system (100) and method for simulating virtual human-body dissection, as compared to prior-arts, provides an accurate representation of human anatomical structures, allowing users to perform virtual dissections and gain tactile insights into the texture and feel of various organs, tissues and structures. Simulation system (100) includes a computing bed (10) with an interactive-display screen (20), a haptic device (30), a graphic rendering device (40), a control unit (50) and processing unit (51). The interactive-display screen (20) enables selection of a region-selection module (20a), a tool-selection module (20b), an anatomical planes and positions module (20c) and a training module (20d) which are operated and viewed by the haptic device (30), a graphic rendering device (40) to perform virtual dissections and gain tactile insights into the texture and feel.

6 Claims, 11 Drawing Sheets

(56) References Cited

U.S. PATENT DOCUMENTS

| | | | |
|---|---|---|---|
| 2018/0200018 A1* | 7/2018 | Silva | A61B 5/066 |
| 2019/0369713 A1* | 12/2019 | Suzuki | G06F 3/011 |
| 2020/0330166 A1* | 10/2020 | Meglan | A61B 17/3423 |
| 2020/0360089 A1* | 11/2020 | Lee | G06N 20/00 |
| 2022/0096164 A1* | 3/2022 | Jarc | A61B 34/35 |

* cited by examiner

SIMULATION SYSTEM FOR VIRTUAL HUMAN-BODY DISSECTION AND METHOD FOR SIMULATING VIRTUAL HUMAN-BODY DISSECTION

FIELD OF THE INVENTION

The present disclosure relates to a learning platform. Particularly, the present disclosure relates to a simulation system and method for performing virtual human-body dissection.

BACKGROUND OF THE INVENTION

The traditional method of learning human medical anatomy is through cadaver dissection. This method has been used for centuries and is still considered to be the gold standard for anatomical education. However, cadaver dissection has a number of drawbacks, for example, cadaver dissection can be expensive and time-consuming to obtain cadavers, cadavers can be difficult to obtain in some parts of the world, cadavers can be a source of infection and some students may have ethical or religious objections to cadaver dissection.

Thus, there is a need for a simulating system and method for simulating virtual human-body dissection.

OBJECTS OF THE INVENTION

Some of the objects of the arrangement of the present disclosure are aimed to ameliorate one or more problems of the prior art or to at least provide a useful alternative and are listed herein below.

A principle object of the present disclosure is to provide a simulating system and method for simulating virtual human-body dissection that simulates realistic virtual dissection procedures by virtual reality (VR), mixed reality (MR) and haptic feedback that provides an accurate representation of human anatomical structures, allowing users to perform virtual dissections and gain tactile insights into the texture and feel of various organs, tissues and structures.

Another object of the present disclosure is to provide a simulating system and method for simulating virtual human-body dissection that aims to overcome the limitations and challenges associated with traditional cadaveric dissection by offering a virtual platform that recreates the process in a detailed and interactive manner.

Still another object of the present disclosure is to provide a simulating system and method for simulating virtual human-body dissection that provides a stress-free environment for dissection and aims to alleviate psychological discomfort and anxiety experiences during known hands-on cadaveric dissection.

Yet another object of the present disclosure is to provide a simulating system and method for simulating virtual human-body dissection that provides systematic approach to learning human-anatomy by categorizing the virtual dissection procedures into step-wise instructions ensuring a comprehensive understanding of anatomical planes, instrument use and the order of dissection.

Another object of the present disclosure is to provide a simulating system and method for simulating virtual human-body dissection that integrates haptic technology to enhance the virtual experience of tactile feedback to perceive the physical characteristics of anatomical structures and organs, closely emulating the sensations of real dissection.

Still another object of the present disclosure is to provide a simulating system and method for simulating virtual human-body dissection that aims to provide a holistic experience that aligns with various medical traditions and practices by incorporating visual of ayurvedic marma points.

Other objects and advantages of the present disclosure will be more apparent from the following description when read in conjunction with the accompanying figures, which are not intended to limit the scope of the present disclosure.

SUMMARY OF THE INVENTION

The present invention discloses a simulation system for virtual human-body dissection, in accordance with the one embodiment of the present invention, that simulate realistic virtual dissection procedures by virtual reality (VR), mixed reality (MR) and haptic feedback for performing virtual dissections and gain tactile insights into the texture and feel of various organs, tissues, and structures. The system includes a computing bed defined with an interactive display screen, a haptic device, a graphic rendering device, a control unit and a processing unit, in which the control unit and the processing unit are defined in the computing bed. The computing bed with the interactive-display screen displays virtual human body based on virtual-reality (VR) and mixed-reality (MR) and defined for interactive simulation. The interactive-display screen is in communication with the computing bed. The interactive-display screen is defined to display a region-selection module, a tool-selection module, an anatomical planes and positions module and a training module. The region-selection module is defined with categories of human anatomical regions and facilitates a user to select a region for dissection. The tool-selection module is defined with a list of dissection tools and provides three-dimensional tool view and understanding. The anatomical planes and positions module to understand planes and positions in a three-dimensional environment of human anatomy. The training module is used for training in holding dissection tools, step-wise buttonhole technique instructions and performance and step-wise dissection instructions and performance for each human anatomical region. Along with the computing bed and virtual 3 D dissection procedure through touch, it is further extended through VR System where the user will be able to experience the real-time dissection procedure with the haptic feedback.

The haptic device, wearable by the user to input instructions of selection of human anatomical region, dissection tool, anatomical planes and positions and dissection instructions and perform virtual dissections. The graphic rendering device, which is in connection with the computing bed, interactive-display screen and the haptic device, to render the user virtual three-dimensional human body. The control unit and the processing unit defined with the computing bed and cooperates with the interactive-display screen, the graphic rendering device, the haptic device. During virtual dissection the control unit signals the interactive-display screen, the graphic rendering device to three-dimensionally view and the haptic device to perform and sense dissection. The graphic rendering device and the haptic device during dissection facilitates the user to experience skin incisions, exposing nerves and layers under skin. Thus, control unit and the processing unit signals the interactive-display screen to display a two-dimensional view and a three-dimensional view, signal the graphic rendering device to render a three-dimensional image for display on the interactive-display screen and signals the haptic device to perform a dissection operation on the three-dimensional image and sense the simulated dissection operation.

In one embodiment, the dissection instructions include marked landmarks for the human anatomical regions to perform skin incisions.

In one embodiment, the dissection instructions include marking marma points on human anatomical regions.

The present disclosure also discloses a method for simulating virtual human-body dissection. The method includes:

providing a simulation system for virtual human-body dissection, the simulation system is defined with a computing bed defined with an interactive display screen to develop a three-dimensional virtual human body based on virtual-reality (VR) and mixed-reality (MR) and defined for interactive simulation, a haptic device wearable by the user to input instructions of selection of human anatomical region, dissection tool, anatomical planes and positions and dissection instructions and perform virtual dissections, a graphic rendering device to render the user virtual three-dimensional human body, a control unit and a processing unit defined with the computing bed:

selecting, by a user, from an interactive module, wherein selection includes:
  a region-selection module which is defined with categories of human anatomical regions and facilitates a user to select a region for dissection;
  a tool-selection module which is defined with a list of dissection tools and provides three-dimensional tool view and understanding;
  an anatomical planes and positions module to understand planes and positions in a three-dimensional environment of human anatomy; and
  a training module for training of holding dissection tools, step-wise buttonhole technique and step-wise dissection instructions for each human anatomical region:

performing, by the user, virtual dissection by selecting dissection tools, selecting planes and positions for dissection, following steps for dissection through the interactive display screen by the graphic rendering device and also a further extension to it by using the haptic device to experience skin incisions, exposing nerves and layers under skin, wherein, the control unit and the processing unit:
  signals the interactive-display screen to display a two-dimensional view and a three-dimensional view;
  signals the graphic rendering device to render a three-dimensional image for display on the interactive-display screen; and
  signals the haptic device to perform a dissection operation on the three-dimensional image and sense the simulated dissection operation.

In one embodiment, the step includes marking landmarks for the human anatomical regions to perform skin incisions as defined in the dissection instructions.

In one embodiment, the marking of marma points on human anatomical regions as defined in the dissection instructions.

BRIEF DESCRIPTION OF ACCOMPANYING DRAWINGS

The present disclosure will now be described with the help of the accompanying drawings, in which.

DETAILED DESCRIPTION OF THE INVENTION

Figure 1:
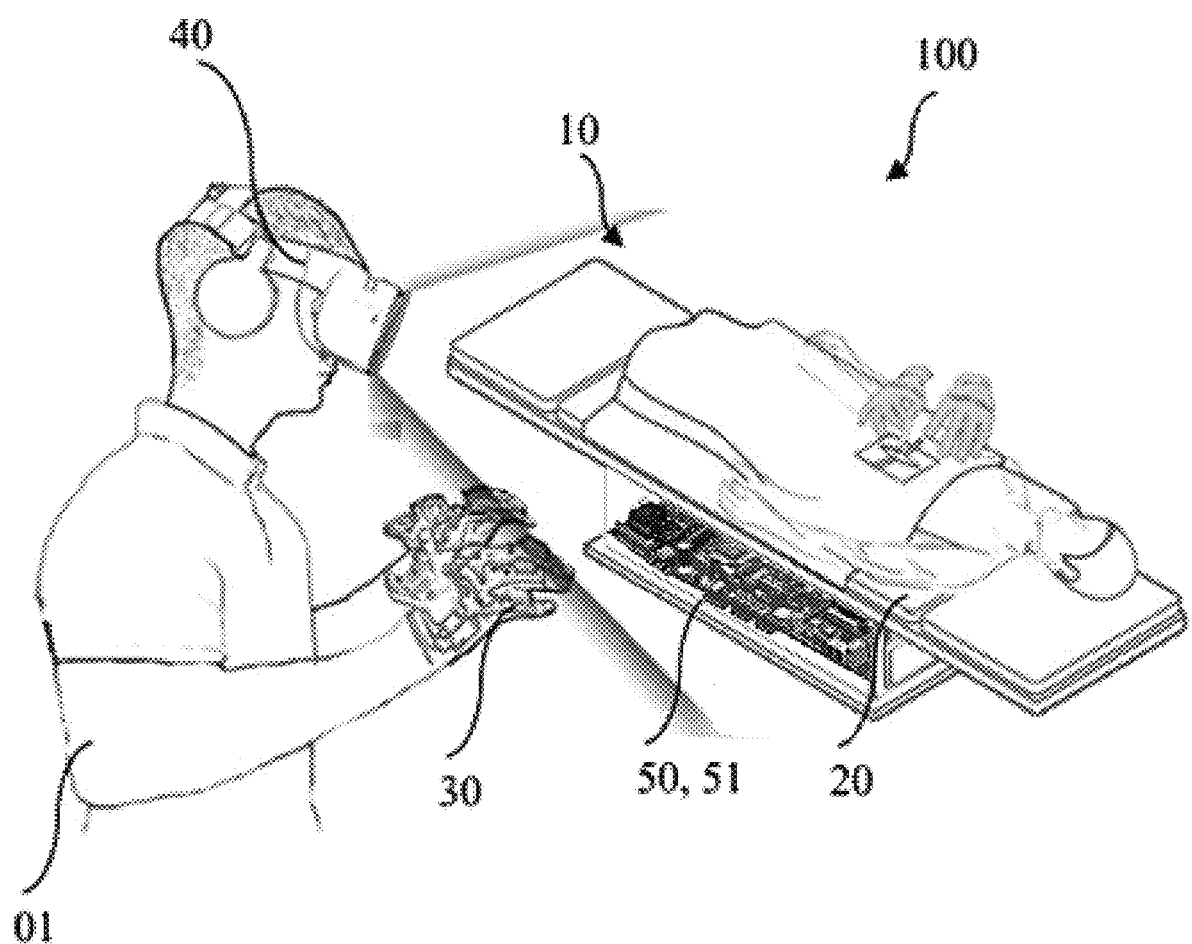
FIG. 1 illustrates a schematic representation of a simulation system (100) for virtual human-body (05) dissection, in accordance with one embodiment of the present disclosure, which includes a computing bed (10), an interactive-display screen (20), a haptic device (30), a graphic rendering device (40), a control unit (50) and a processing unit (51)

Referring now to the drawings, FIG. 1 to 15, where the present invention is generally referred to with numeral (100), it can be observed that a simulation system for virtual human-body dissection, in accordance with an embodiment, is provided which includes a computing bed (10), an interactive-display screen (20), a haptic device (30), a graphic rendering device (40) and a control unit (50).

Figure 12:
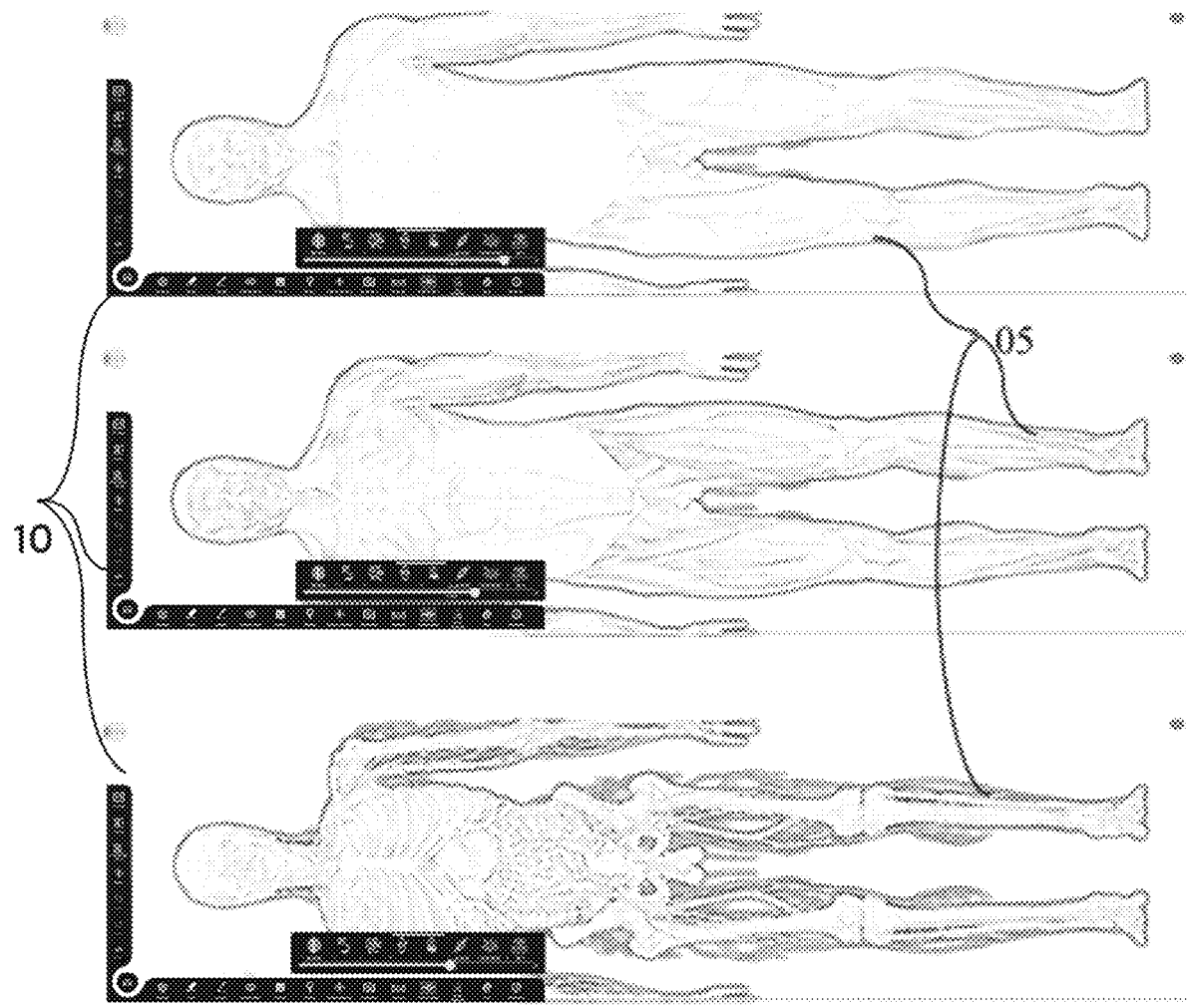
FIG. 12 illustrates various schematic representations of three dimensional internal views of human anatomical regions to enable understanding.
Figure 13:
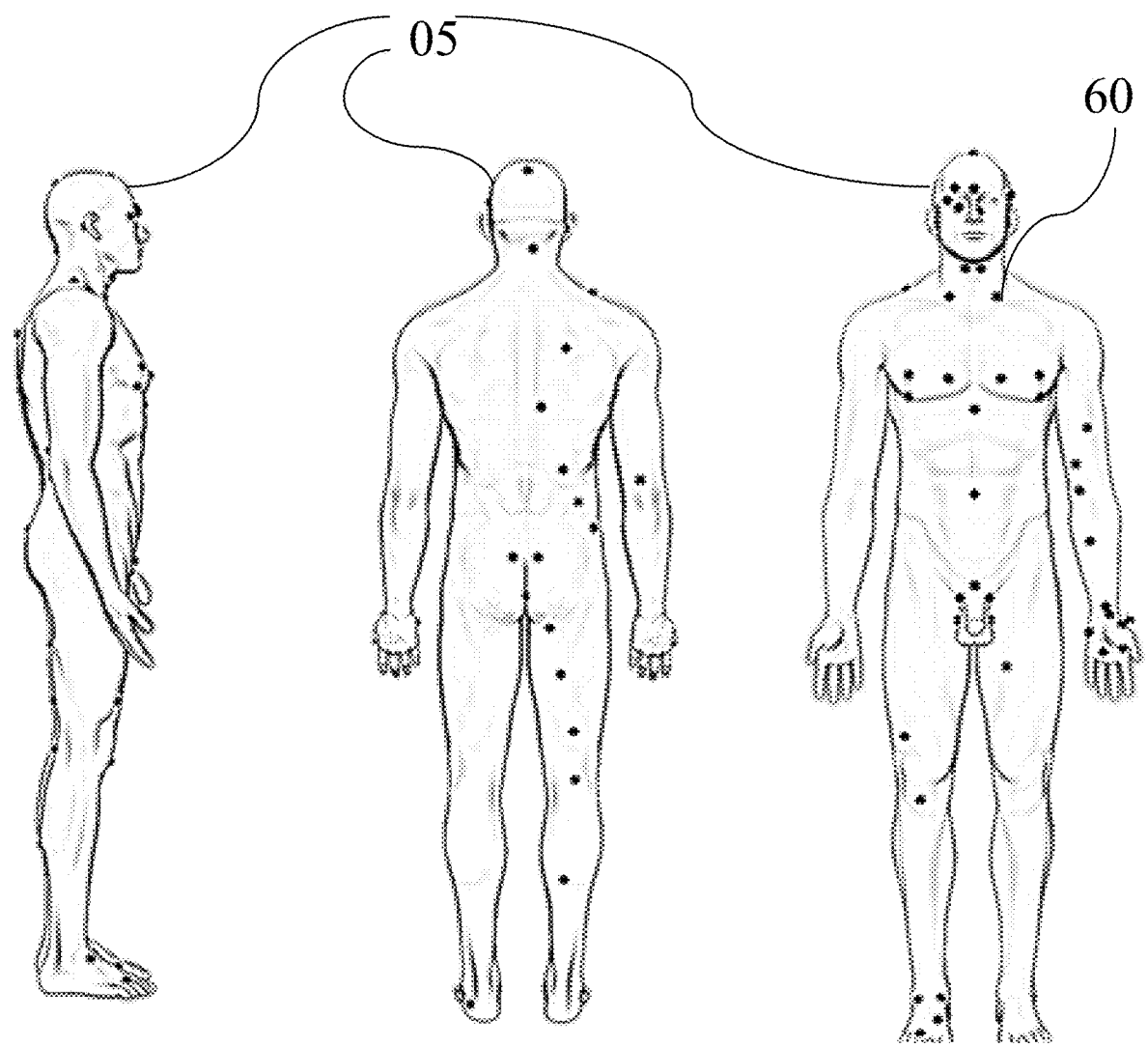
FIG. 13 illustrates schematic representations of marking marma points on human anatomical regions.
Figure 14:
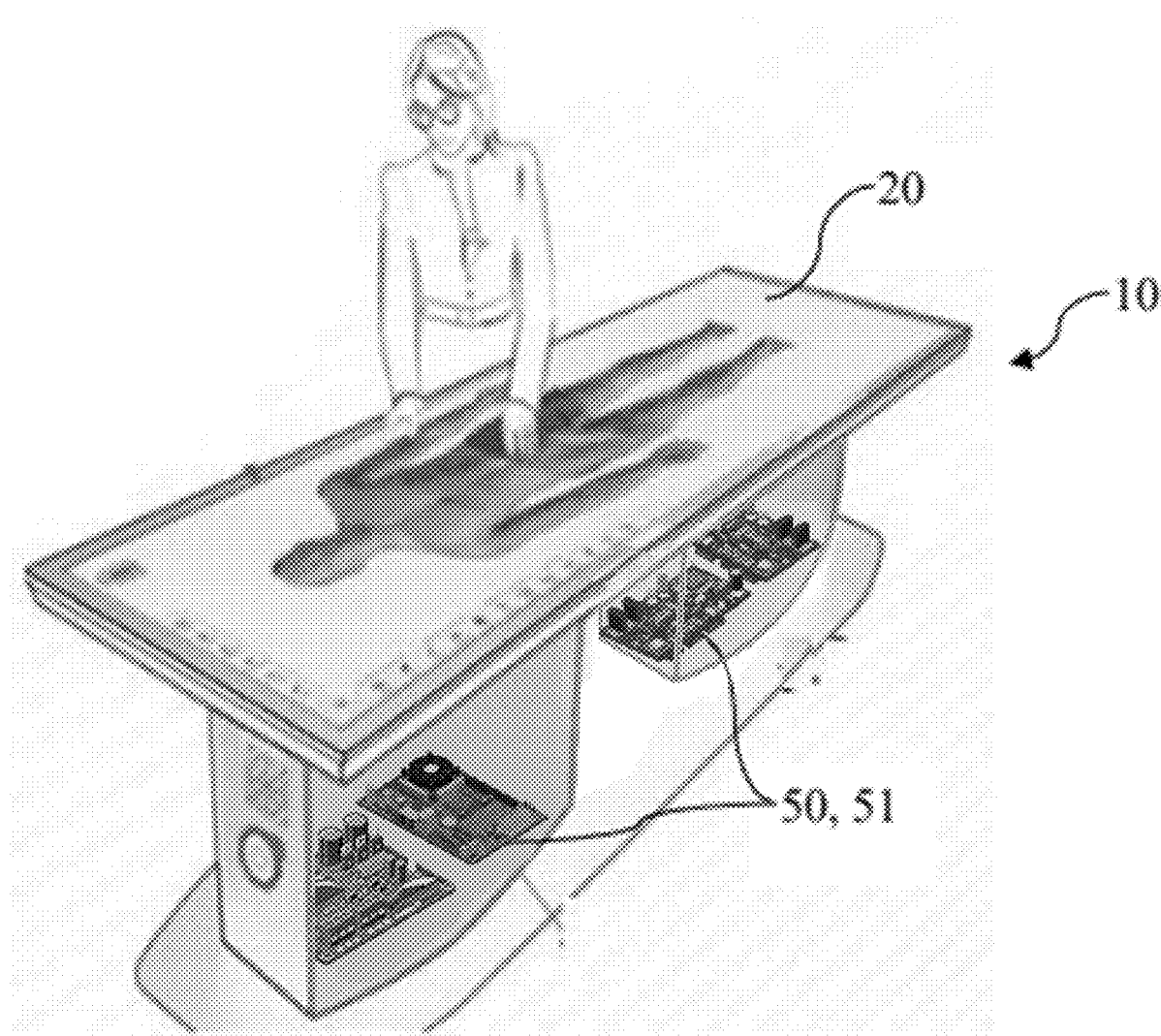
FIG. 14 illustrates an interactive-display screen (20) illustrating a three-dimensional view of human anatomy.
Figure 15:
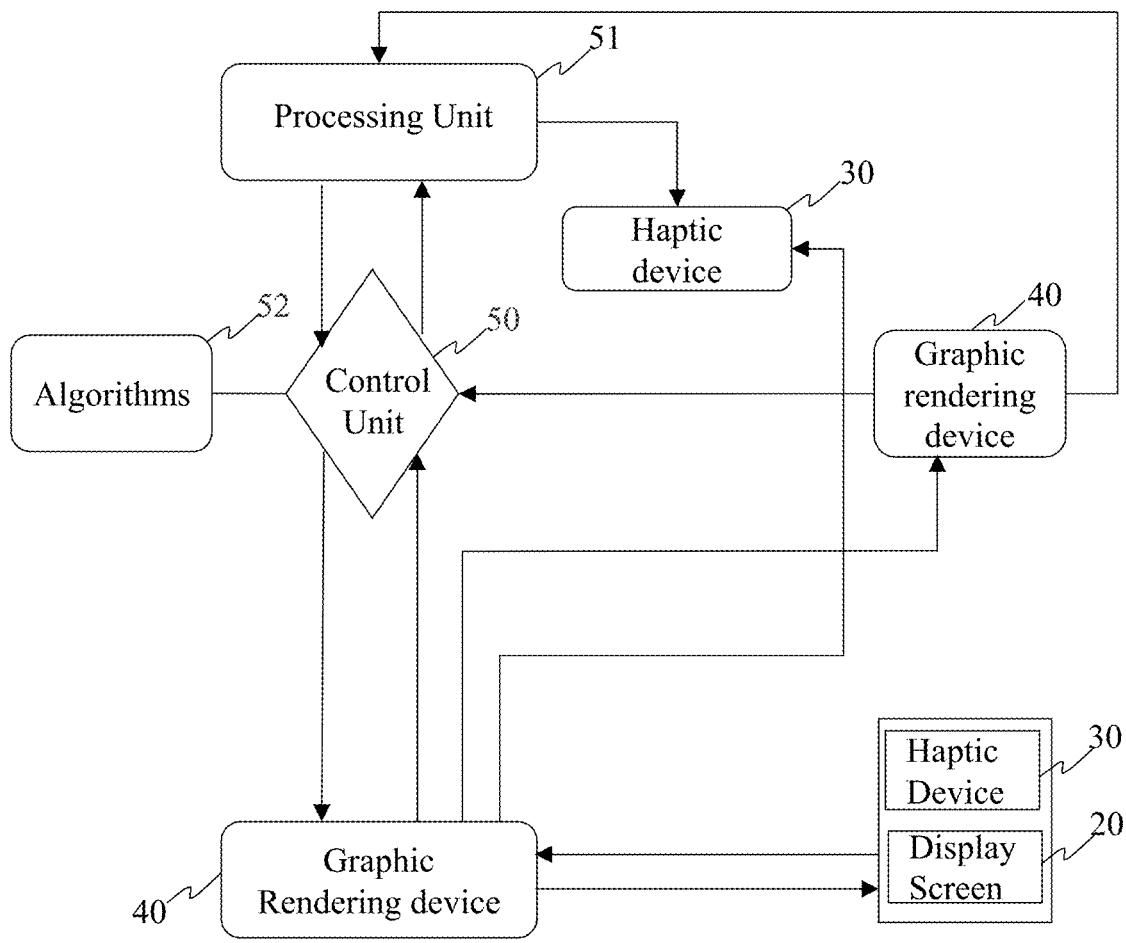
FIG. 15 illustrates a flow-chart of interaction between a computing bed (10), an interactive-display screen (20), a haptic device (30), a graphic rendering device (40) and a control unit (50) and a processing unit (51).

The computing bed (10) is defined with an interactive-display screen (20) to display virtual human-body (05) based on virtual-reality (VR) and mixed-reality (MR) and defined for interactive simulation. The computing bed (10) has screen that is in form of bed to view the human anatomy and thus is a digital bed. Parts and components of a known computer are embedded in the computing bed (10). The computing bed (10) displays three-dimensional internal views of human anatomical regions, as shown in FIG. 12 to enable understanding and three-dimensional view by using the graphic rendering device (40). Though, the present disclosure discloses two-dimensional view or three-dimensional view, however, the present disclosure is not limited to two-dimensional view or three-dimensional view and more than three-dimensional view like four-dimensional view is included with appropriate known devices. The interactive-display screen (20) is defined to display a region-selection module (20a), a tool-selection module (20b), an anatomical planes and positions module (20c) and a training module (20d).

Figure 2:
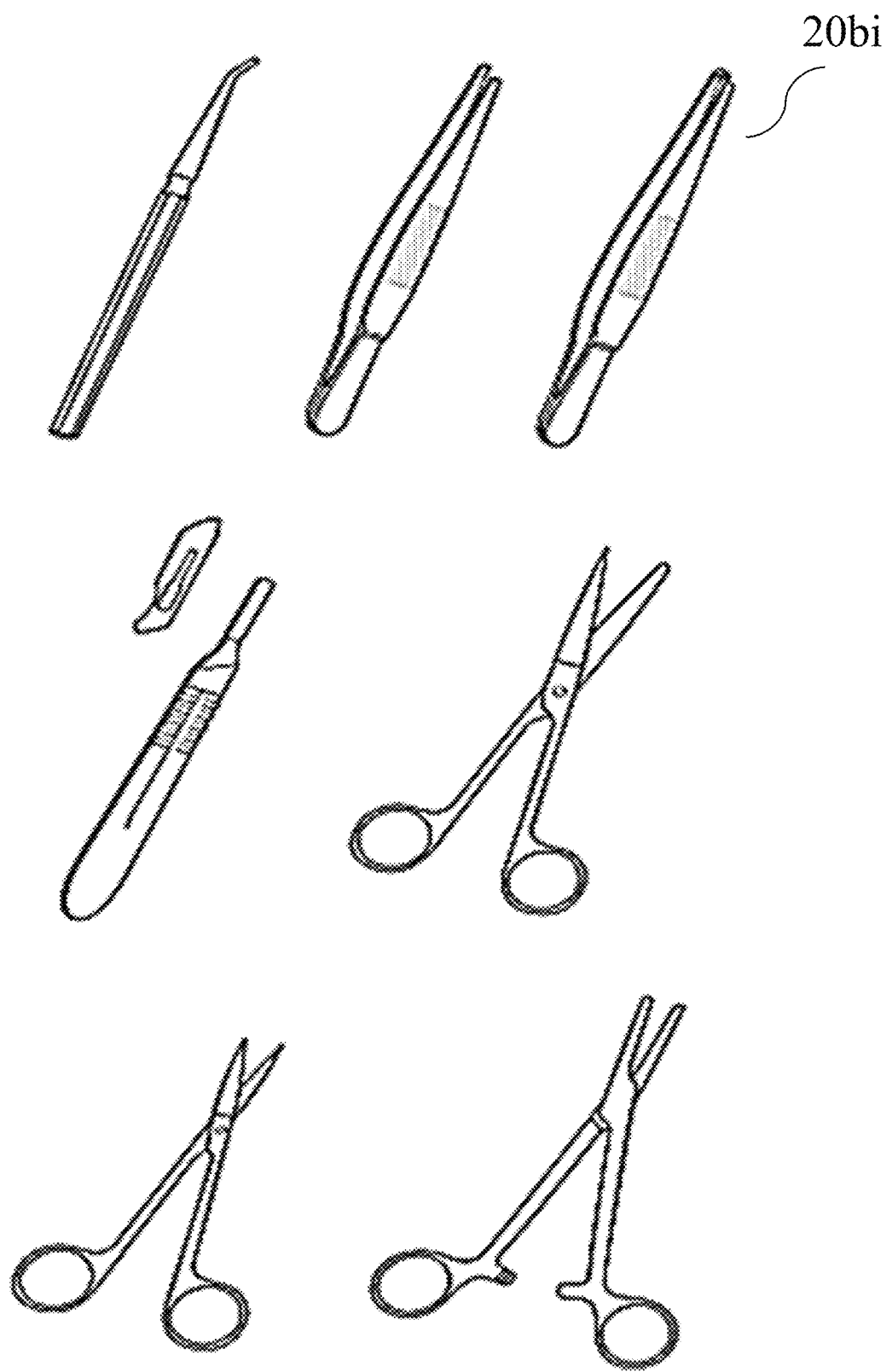
FIG. 2 illustrates a schematic representation of a tool-selection module (20b) of the interactive-display screen (20)
Figure 3:
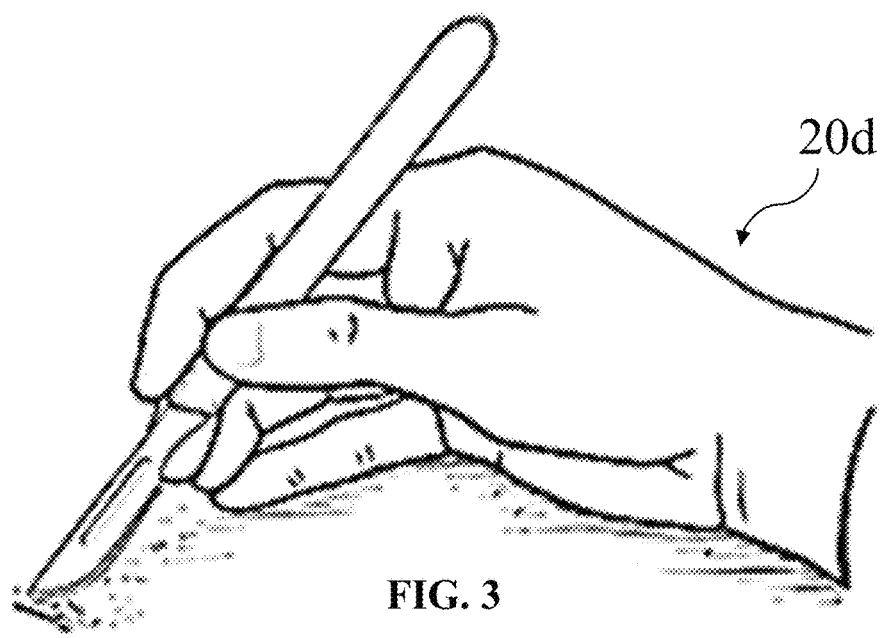
FIG. 3 illustrates a schematic representation of holding a tool by using the tool-selection module (20b)
Figure 4:
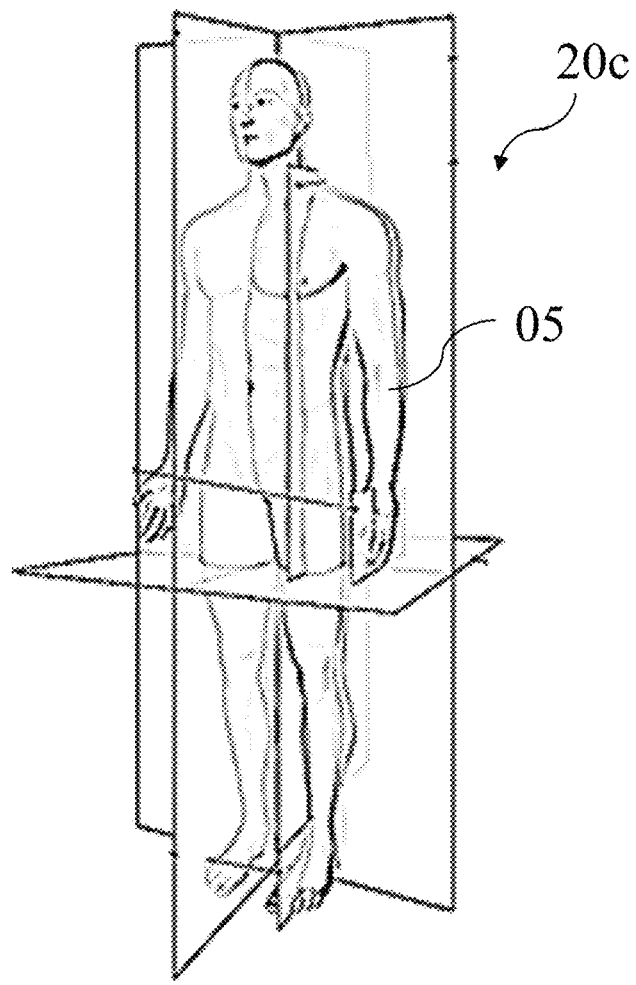
FIG. 4 illustrates a schematic representation of marked planes and position in the anatomical planes and positions module (20c)
Figure 5:
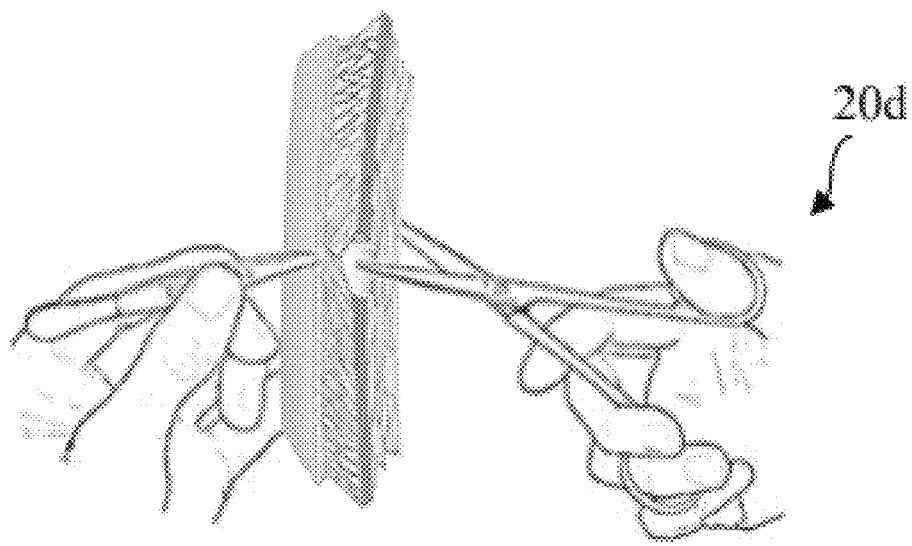
FIG. 5 illustrates a schematic representation of virtual handling dissection tools and performing dissection.
Figure 6:
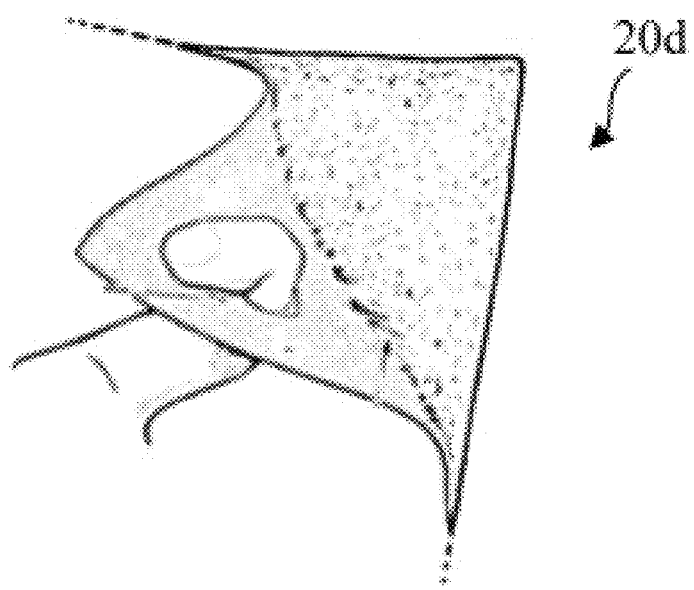
FIG. 6 illustrates a schematic representation of a virtual skin incision.
Figure 7:
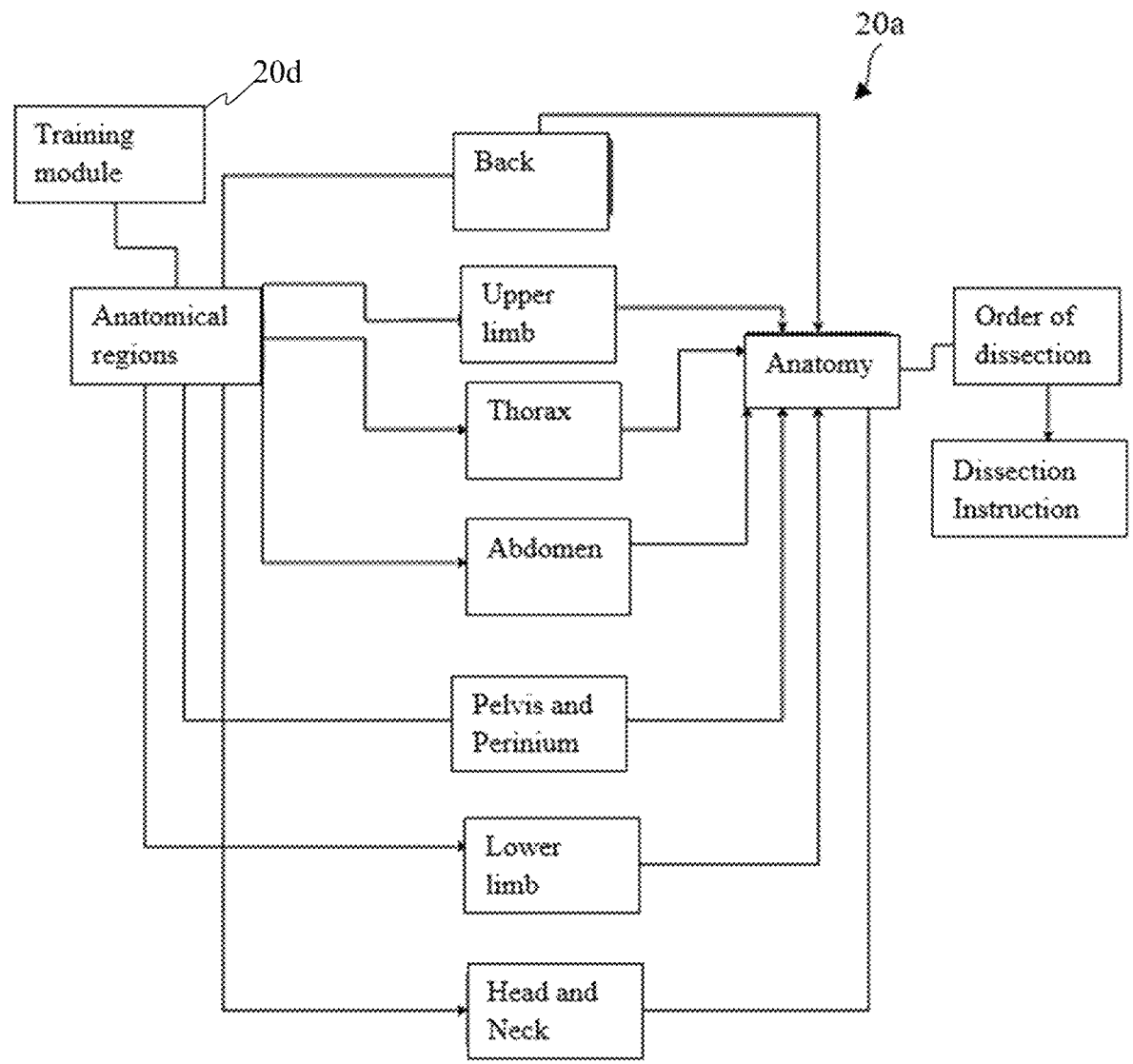
FIG. 7 illustrates a flowchart depicting different modules for human anatomical region to view step-wise dissection instructions and performances.
Figure 8:
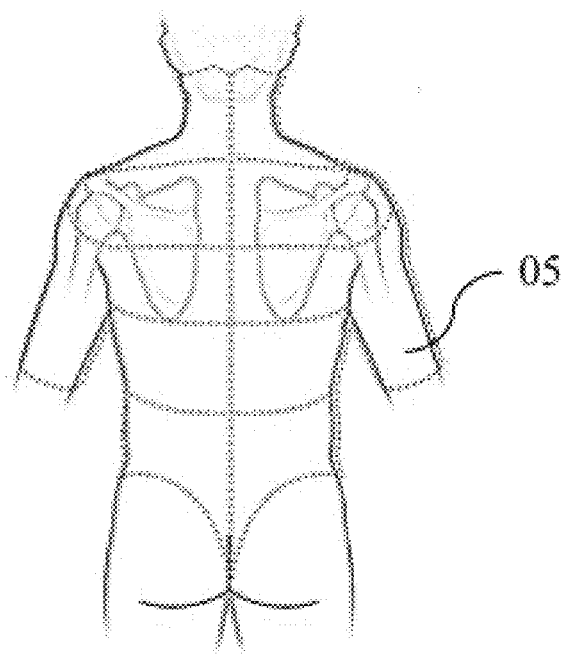
FIGS. 8 and 9 illustrates a schematic representation of marked landmarks for the human anatomical regions to perform skin incisions.
Figure 9:
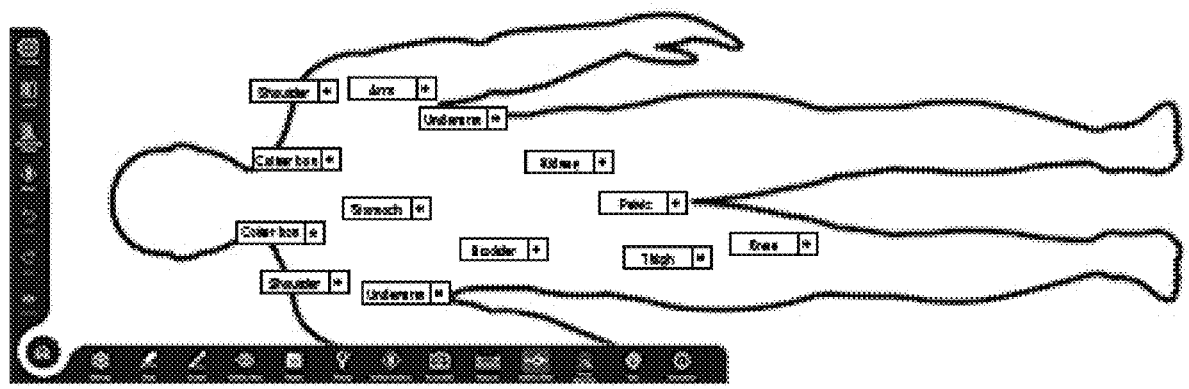
Figure 10:
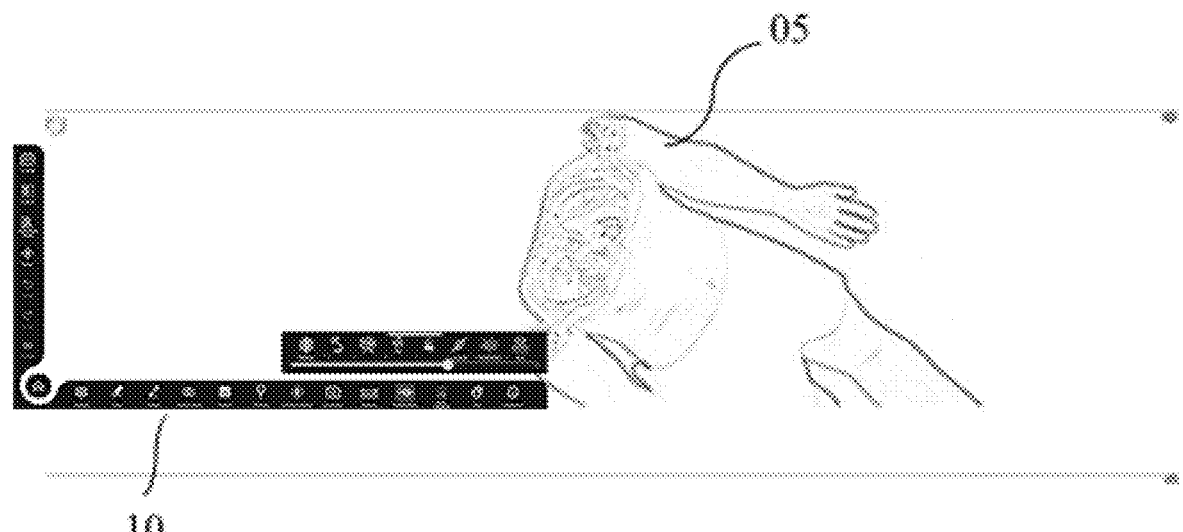
FIGS. 10 and 11 illustrate a schematic representation of various human anatomical region at different angles to view during dissection.
Figure 11:
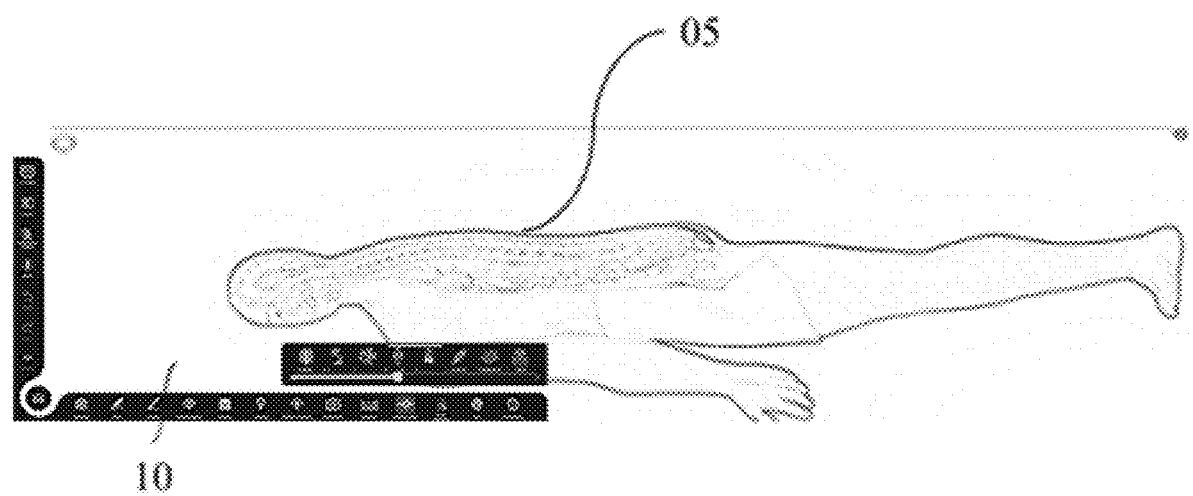

The region-selection module (20a) is defined with categories of human anatomical regions and facilitates a user (01) to select a region for dissection. Some regions of the region-selection module (20a) are illustrated in the flowchart of FIG. 7. The tool-selection module (20b) defined with a list of dissection tools (20bi) and provides three-dimensional tool view and understanding. FIG. 2 illustrates some of the dissection tools (20bi) which are provided in the tool selection module (20b). The anatomical planes and positions module (20c) to understand planes and positions in a three-dimensional environment of human anatomy. FIGS. 8 and 9 depicts planes selected for a human anatomy in the anatomical planes and positions module (20c). The training module (20d) for training of holding dissection tools, step-wise buttonhole technique instructions and performance and step-wise dissection instructions and performances for each human anatomical region. The region-selection module (20a), the tool-selection module (20b), the anatomical planes and positions module (20c) and the training module (20d) are provided with different computerized features like zoom-in and zoom-out, rotation/revolution, cross-sections of the three-dimensional virtual human body enabling the user to view the internal parts of the human body under observation as shown in FIGS. 10 and 11, changing color of text or model, inserting markings and similar other known features in field of computer. The input for selecting features can be performed by known input devices like keypad or touchpad, mouse, stylus, voice command through mic attached either to the computing bed (10), the interactive-display screen, the haptic device (30) and the graphic rendering device (40). Also, inputs can be received from the haptic device (30). Along with the computing bed (10) and virtual 3 D dissection procedure through touch, it is further extended through VR System where the user will be able to experience the real-time dissection procedure with the haptic feedback.

The haptic device (30) is wearable by the user (01) to input instructions of the selection of human anatomical regions, dissection tools, anatomical planes and positions and dissection instructions and perform virtual dissections. The haptic device (30) allows users (01) to perform virtual dissections and gain tactile insights into the texture and feel of various organs, tissues and structures and thus provide tactile feedback to perceive the physical characteristics of anatomical structures and organs, closely emulating the sensations of real dissection.

The graphic rendering device (40) is in connection with the computing bed (10), interactive-display screen (20) and the haptic device (30), to render the user (01) virtual three-dimensional virtual human body (05). Typically, the graphic rendering device (40) is oculus or similar other known graphic renderers.

The control unit (50) and a processing unit (51) is defined with the computing bed (10) and the control unit (50) and the processing unit (51) cooperates with the interactive-display screen (20), the graphic rendering device (40), the haptic device (30) and during virtual dissection the control unit (50) signal the interactive-display screen (20) and the graphic rendering device (40) to three-dimensionally view and the haptic device (30) to perform and sense dissection. The graphic rendering device (40) and the haptic device (30) during dissection facilitates the user (01) to experience skin incisions, exposing nerves and layers under skin. The control unit (50) and the processing unit (51) signals the interactive-display screen (20) to display a two-dimensional view and a three-dimensional view; signals the graphic rendering device (40) to render a three-dimensional image for display on the interactive-display screen (20) and signals the haptic device (30) to perform a dissection operation and sense the simulated dissection operation. Moreover, the processing unit (51) is defined with algorithms (52) that works based on the sensed information from the haptic device (30) and the instruction received from said interactive-display screen (20). The algorithms (52) connects the real-time feedback from the haptic device (30) and accordingly enables the processing unit (51) to signal the control unit (50) to perform various dissections and surgical simulations for three-dimensional interaction.

In additional embodiment, dissection instructions include marked landmarks for the human anatomical regions to perform skin incisions.

In additional embodiment, dissection instructions includes marking marma points (60) on human anatomical regions.

The present disclosure also discloses a method for simulating virtual human-body (05) dissection, in accordance with one embodiment of the present disclosure. The best-method includes providing the simulation system (100) for virtual human-body (05) dissection. The simulation system (100) is defined with the computing bed (10) defined with the interactive display screen (20), the haptic device (30), the graphic rendering device (40), the control unit (50) and the processing unit (51) of the computing bed (10): the computing bed (10) facilitate to develop a three-dimensional virtual human body (05) based on virtual-reality (VR) and mixed-reality (MR) and is defined for interactive simulation, the haptic device (30) is wearable by the user (01) to input instructions of selection of human anatomical regions, dissection tools, anatomical planes and positions and dissection instructions and perform virtual dissections, the graphic rendering device (40) to render the user virtual three-dimensional human body, the control unit (50) and the processing unit (51) as described in above paragraphs and not repeated to avoid unwanted repetition.

The next method step is selecting, by the user (01), from the interactive module (20). The region-selection module (20a) is defined with categories of human anatomical regions and facilitates a user to select the region for dissection. The tool-selection module (20b) is defined with a list of dissection tools and provides three-dimensional tool view and understanding. The anatomical planes and positions module (20c) to understand planes and positions in a three-dimensional environment of human anatomy. The training module (20d) for training of holding dissection tools, step-wise buttonhole technique and step-wise dissection instructions for each human anatomical region.

The next step is performing, by the user (05), virtual dissection by selecting dissection tools, selecting planes and positions for dissection, following steps for dissection by the graphic rendering device (40) and the haptic device (30) to experience skin incisions, exposing nerves and layers under skin. In which, the control unit (50) and the processing unit (51) defined to:

signal the interactive-display screen (20) to display a two-dimensional view and a three-dimensional view;

signal the graphic rendering device (40) to render a three-dimensional image for display on the interactive-display screen (20); and signal the haptic device (30) to perform a dissection operation on the three-dimensional image and sense the simulated dissection operation.

In one embodiment, the method includes marking landmarks for the human anatomical regions to perform skin incisions as defined in the dissection instructions. In an additional embodiment, the method includes marking of marma points (60) on human anatomical regions as defined in the dissection instructions.

The foregoing description conveys the best understanding of the objectives and advantages of the present invention. Different embodiments, steps or alternatives may be made of the inventive concept of this invention. It is to be understood that all matter disclosed herein is to be interpreted merely as illustrative, and not in a limiting sense.

What is claimed is:

1. A simulation system (100) for virtual human-body (05) dissection, comprising:
    a computing bed (10) defined with an interactive display screen (20), to display a virtual human-body (05) based on virtual-reality (VR) and mixed-reality (MR) and defined for interactive simulation, said interactive-display screen (20) defined to display:
        a region-selection controller (20a) defined with categories of human anatomical regions and facilitates a user (01) to select a region for dissection;
        a tool-selection controller (20b) defined with a list of dissection tools (20bi) and provides three-dimensional tool view and understanding;
        an anatomical planes and positions controller (20c) to understand planes and positions in a three-dimensional environment of human anatomy; and
        a training controller (20d) for training users in holding dissection tools, providing step-wise buttonhole technique instructions and performance and providing step-wise dissection instructions and performances for each human anatomical region;
    a haptic device (30), wearable by the user (01) to input instructions of the selection of human anatomical regions, dissection tools, anatomical planes and positions and dissection instructions and perform virtual dissections;
    a graphic rendering device (40), in connection with said computing bed (10), interactive-display screen (20) and said haptic device (30), to render the user (01) virtual three-dimensional virtual human body (05); and
    a control unit (50) and a processing unit (51) defined with said computing bed (10) and cooperates with said computing bed (10), said interactive-display screen (20), said graphic rendering device (40) to provide a user with a simulated dissection experience, wherein during virtual dissection, said control unit (50) and said processing unit (51) are configured to:
        signal the interactive-display screen (20) to display a two-dimensional view and a three-dimensional view;
        signal the graphic rendering device (40) to render a three-dimensional image for display on the interactive-display screen (20); and
        signal the haptic device (30) to perform a dissection operation on the three-dimensional image and sense the simulated dissection operation.

2. The simulation system (100) for virtual human-body dissection as claimed in claim 1, wherein said dissection instructions include marked landmarks for the human anatomical regions to perform skin incisions.

3. The simulation system (100) for virtual human-body dissection as claimed in claim 1, wherein said dissection instructions includes marking marma points (60) on human anatomical regions.

4. A method for simulating virtual human-body (05) dissection, comprising:
    providing a simulation system (100) for virtual human-body (05) dissection, said simulation system (100) defined with a computing bed (10) defined with an interactive display screen (20) to develop a three-dimensional virtual human body (05) based on virtual-reality (VR) and mixed-reality (MR) and defined for interactive simulation, a haptic device (30), wearable by the user (01), to input instructions of selection of human anatomical regions, dissection tools, anatomical planes and positions and dissection instructions and perform virtual dissections, a graphic rendering device (40) to render the user virtual three-dimensional human body, a control unit (50) and a processing unit (51) defined with said computing bed (10);
    selecting, by the user (01), from the interactive display screen (20), wherein selection includes:
        a region-selection controller (20a) defined with categories of human anatomical regions and facilitates a user to selected a region for dissection;
        a tool-selection controller (20b) defined with a list of dissection tools and provides three-dimensional tool view and understanding;
        an anatomical planes and positions controller (20c) to understand planes and positions in a three-dimensional environment of human anatomy; and
        a training controller (20d) for training users in holding dissection tools, providing step-wise buttonhole technique and providing step-wise dissection instructions for each human anatomical region; and
    performing, by the user (05), virtual dissection by selecting dissection tools, selecting planes and positions for dissection, following steps for dissection by said graphic rendering device (40) and said haptic device (30) to experience skin incisions, exposing nerves and layers under skin;
    wherein, said control unit (50) and said processing unit (51) are configured to:
        signal the interactive-display screen (20) to display a two-dimensional view and a three-dimensional view;
        signal the graphic rendering device (40) to render a three-dimensional image for display on the interactive-display screen (20); and
        signal the haptic device (30) to perform a dissection operation on the three-dimensional image and sense the simulated dissection operation.

5. The method for simulating virtual human-body dissection as claimed in claim 4, includes marking landmarks for the human anatomical regions to perform skin incisions as defined in said dissection instructions.

6. The method for simulating virtual human-body dissection as claimed in claim 4, includes marking of marma points (60) on human anatomical regions as defined in said dissection instructions.

* * * * *